United States Patent [19]

Daum et al.

[11] 4,086,237

[45] Apr. 25, 1978

[54] METHOD OF PREPARING 3-METHYL PYRIDINE

[75] Inventors: Gerhard Daum, Cologne; Hermann Richtzenhain, Much-Schwellenbach, both of Germany

[73] Assignee: Dynamit Nobel Aktiengesellschaft, Troisdorf Bez. Cologne, Germany

[21] Appl. No.: 681,100

[22] Filed: Apr. 28, 1976

[30] Foreign Application Priority Data

May 2, 1975 Germany .............................. 2519529

[51] Int. Cl.² ........................................... C07D 213/06
[52] U.S. Cl. ................................................ 260/290 P
[58] Field of Search ..................................... 260/290 R

[56] References Cited

U.S. PATENT DOCUMENTS

| 3,828,051 | 8/1974 | Kusunoki et al. | 260/290 P |
| 3,829,428 | 8/1974 | Hargis | 260/290 P |

Primary Examiner—Alan L. Rotman
Attorney, Agent, or Firm—Burgess, Dinklage & Sprung

[57] ABSTRACT

3-methyl pyridine is produced by catalytic, e.g. palladium, dehydrogenation of 2-methyl-1,5-diaminopentane or a mixture thereof with 3-methyl piperidine, at 200°–400° C.

9 Claims, No Drawings

METHOD OF PREPARING 3-METHYL PYRIDINE

BACKGROUND

The present invention relates to a method of preparing 3-methyl pyridine from 2-methyl-1,5-diaminopentane or from a mixture of 2-methyl-1,5-diaminopentane and 3-methyl piperidine.

3-Methyl pyridine can be obtained by the reaction of aliphatic aldehydes with ammonia. (Chem. Techn. 22 (1970) 679–80, 745–48; J. pr. Chem. 312 (1970) 849–52).

It is furthermore known that pyridine or substituted pyridines can be prepared by the dehydrogenation of piperidine or suitably substituted piperidines.

Thus, German Pat. No. 1,192,648 describes the preparation of pyridine from piperidine with the use of a palladium-containing catalyst. Platinum and nickel are also described as usable catalysts in the same publication.

According to T. Takata, Bull. Chem. Soc. Japan 35, (1962) No. 9, pages 138–43, 3-methyl pyridine can similarly be obtained by dehydrogenation from 3-methyl piperidine.

For the preparation of the starting compound 3-methyl piperidine, 2-methyl glutaric acid nitrile is reacted with sodium amide to produce methyl glutaroimidine, and this is treated with sodium, whereupon the formation of 3-methyl piperidine takes place via 3-methyl-2,6-diaminopiperidine as an intermediate product.

This complex laboratory method is theoretically interesting, but it is not practical for production in technical quantities.

THE INVENTION

It has now been found possible to produce 3-methyl pyridine directly from 2-methyl-1,5-diaminopentane. The chemical reaction consists in a cyclization of the aliphatic diamine with the liberation of ammonia and the simultaneous dehydrogenation of the intermediately formed 3-methyl piperidine to form the aromatic pyridine system.

The subject matter of the invention is therefore a method of preparing 3-methyl pyridine, which is characterized in that 2-methyl-1,5-diaminopentane or a mixture of 2-methyl-1,5-diaminopentane and 3-methyl piperidine is treated with a dehydrogenation catalyst at temperatures between 200 and 400° C.

A preferred embodiment of the method of the invention is the use of a hydrogenation product of 2-methyl glutaric acid dinitrile as the starting substance in accordance with U.S. application Ser. No. 670,200, Mar. 25, 1976. This hydrogenation product always contains 2-methyl-1,5-diaminopentane and 3-methyl piperidine. The ratio of the two products can vary widely according to the hydrogenation conditions. The separation of the two components is unnecessary in the method of the invention.

The mixtures of 2-methyl-1,5-diaminopentane and 3-methyl piperidine can contain the latter in proportions of as little as about 0.01 to 0.5% by weight to such large proportions as, say, 95 to 98% by weight. On account of their easy availability, mixtures containing 70 to 90% 3-methyl piperidine by weight and, on the other hand, 70 to 90% 2-methyl-1,5-diaminopentane by weight, are preferred.

Effective catalysts are noble metal catalysts of the platinum group and of the iron group, palladium being greatly preferred, although platinum and nickel can also be useful. The catalyst can be Fe, Co, Ni, Ru, Rh, Pd, Os, Ir, Pt or a mixture thereof.

The catalysts are preferably supported on a suitable support such as aluminum oxide, kieselgur, pumice or the like, and can contain the metals generally in amounts of about 0.2 to 12% by weight. The amount of the catalyst with respect to the starting materials is not critical, although the amounts and the layer thickness should suffice for complete reduction.

Reactors having fixedly mounted or movable catalyst can be used. A catalyst bed through which the starting materials flow in gaseous form is preferred.

The new method is easy to practice, and the end product can be obtained by distillation of the reaction mixture, without complicated refining methods. Incompletely reacted 3-methyl piperidine is separated from the 3-methyl pyridine and recycled.

The reaction takes place in a reactor filled with the catalyst, and can be performed at normal pressure, a low overpressure, or a weak vacuum, generally at pressures of about 10 to 10,000 Torr (mm ozHg), preferably in the range from about 100 to 1500 Torr (mm ozHg).

It appears from the results of experiments that it is preferably to operate in the pressure range below 500 Torr (mm of Hg), because then the reaction product and the $NH_3$ forming as a by-product are rapidly removed from the catalyst bed, leaving the catalyst surface free for additional starting material.

The reaction temperature can vary within a certain range, but it is to be adjusted such that not only will the aliphatic diamine be completely reacted, but also the aromatization of the 3-methyl piperidine already contained in the starting material or formed as an intermediate product will be as complete as possible. Whereas deficient transformation and poor aromatization are the consequences of an excessively low reaction temperature, excessively high reaction temperatures lead to an increased formation of highboiling, discolored condensation products.

Temperatures between 250° and 350° C have proven desirable.

The 3-methyl pyridine that is prepared can serve for the production of pyridine derivatives, especially nicotinic acid.

EXAMPLES

Experimental Arrangement

An upright quartz tube of 25 mm diameter, provided with external electrical heating, was filled with tableted catalyst material and provided with a temperature sensing probe terminating in the center of the 400 mm long catalyst bed.

Above the catalyst layer there was mounted a dropping funnel which was provided with a pressure compensating device and through which the starting material could be fed into the reactor. The bottom end of the quartz tube was connected to a two-necked flask serving as a receiver and surmounted by a water-cooled reflux condenser.

The receiver was cooled with ice. The gases which were not condensed in the reflux condenser were delivered through a cold trap (acetone-dry ice) to the vacuum pump.

EXAMPLE 1

64.5 g of a mixture of amines containing 91.4% = 59 g of 2-methyl-1,5-diaminopentane was fed over a period of 260 minutes into the reactor filled with a catalyst containing 5% palladium on $Al_2O_3$, at a temperature of 300° C and a pressure of 300 Torr (mm of Hg).

45.5 g of the reaction mixture condensed in the receiver, and was analyzed by gas chromatography without further processing.

Analysis:
 7.50% 3-methylpiperidine = 3.42 g
 82.34% 3-methyl pyridine = 37.50 g
 10.16% unknown substances.

From this it appears that, with a complete reaction of 2-methyl-1,5-diaminopentane, the yield of
 3-methylpyridine is 79.3% of the theory
 3-methylpiperidine is 6.8% of the theory.

EXAMPLE 2

The experiment was performed in the apparatus described in Example 1, with the same catalyst.

A mixture of 80 g of 2-methyl-1,5-diaminopentane and 20 g of 3-methyl piperidine was fed into the reactor over a period of 375 minutes at a temperature of 300° C and a pressure of 300 Toor (mm of Hg).

72.5 g of the reaction mixture condensed in the receiver and had the following composition:
 5.74% 3-methyl piperidine = 4.16 g
 89.11% 3-methyl pyridine = 64.6 g
 5.15% unknown substances containing a trace of 2-methyl-1,5-diaminopentane.

Of the compounds put in, therefore, the 2-methyl-1,5-diaminopentane had been reacted virtually completely, and 4.16 g of 3-methyl piperidine had been separated by distillation and recovered and added to the next batch.

The yield with respect to the transformation is 82%.

Similar results were obtained with a palladium catalyst of 6 wt.-% Pd on Kieselgur at a temperature of 280° C and 250 Torr (mm of Hg).

EXAMPLE 3

With the use of the same apparatus and the same catalyst as in Example 1, a mixture of
 12.1 g of 2-methyl-1,5-diaminopentane and 48.4 g of 3-methyl piperidine was fed into the reactor over a period of 310 minutes at 300° C and 300 Torr (mm of Hg).
47.5 g of the reaction mixture condensed in the receiver and had the following composition:
 0.8% 3-methyl piperidine = 0.38 g
 96.53% 3-methyl pyridine = 45.9 g
 2.67% unknown substances still containing a trace of 2-methyl-1,5-diaminopentane.

The 2-methyl-1,5-diaminopentane in the starting mixture had been vitually completely transformed, and more than 99% of the 3-methylpiperidine had been transformed. The yield with respect to the transformation was 83.5%.

When the reaction was repeated under the same conditions described above, but at 330° C and a pressure of 400 Torr (mm Hg), a virtually complete transformation was again achieved.

EXAMPLE 4

Example 1 was repeated, the starting material being a mixture of amines containing 92.5% 2-methyl-1,5-diaminopentane and 0.2% 3-methyl piperidine, and the same results were achieved.

EXAMPLE 5

A vertically disposed pressure tube of a capacity of 0.5 liter, filled with 0.3 l (280 g) of cobalt catalyst type RCH 45/20 Co, tablets 5 × 6 mm (mfr. Fabwerke Hoechst) is purged of air with nitrogen and hydrogen gas is pumped in to a pressure of 400 atmospheres. Then, 70 ml of 2-methylglutaric acid dinitrile and 720 ml of liquid ammonia are proportioned hourly into the bottom of the tube, while a temperature of 110° C is maintained. A pressure of 400 atmospheres is maintained by the replacement of the hydrogen as it is consumed. The hydrogen is circulated for the removal of the reaction heat. The reaction mixture emerging from the reactor passes through a cooling coil into a receiver from which it is taken continuously. After removal of ammonia by distillation, 70 ml per hour is obtained of a mixture which, according to gas chromatographic analysis, contains 90.9% of 2-methyl-1,5-diaminopentane and 8.2% of 3-methylpiperidine, as well as 1 to 2% of more highly condensed secondary and tertiary amines.

EXAMPLE 6

If the procedure of Example 5 is repeated, and if, instead of the catalyst used in Example 1, the same volume (= 240 g) of nickel catalyst type RCH 55/10, tablets 5 × 6 mm (mfr. Hoechst AG) is used, a reaction mixture is obtained which, after analogous processing, is composed of 3.9% 2-methyl-1,5-diaminopentane and 90.1% 3-methylpiperidine. The more highly condensed polyamines amount to from 6 to 8%.

What is claimed is:

1. Process for production of 3-methyl pyridine comprising contacting a material of the group of 2-methyl-1,5-diaminopentane and a mixture of 2-methyl-1,5-diaminopentane and 3-methyl piperidine with a dehydrogenation catalyst for the reaction at a temperature of 200°–400° C, the catalyst being palladium supported on a suitable support, the support containing the catalyst in amount of about 0.2 to 12% by weight.

2. Process of claim 1, wherein a hydrogenation product of 2-methyl glutaric acid dinitrile comprising 2-methyl-1,5-diaminopentane and 3-methyl piperidine, is employed as said material.

3. Process of claim 1, wherein the pressure is 10–10,000 Torr (mm of Hg).

4. Process of claim 1, wherein 3-methyl piperidine is contained in the dehydrogenation product and is separated therefrom, and thereafter contacted with dehydrogenation catalyst at 200°–400° C for formation of 3-methyl pyridine.

5. Process of claim 1, wherein 3-methyl piperidine is contained in the dehydrogenation product and is separated therefrom, and thereafter is recycled to said contacting step.

6. Process of claim 1, wherein the pressure is 100–1500 Torr (mm of Hg) and the catalyst is palladium.

7. Process of claim 6, wherein the pressure is 100–500 Torr (mm of Hg).

8. Process of claim 1, wherein the support is aluminum oxide, Kieselgur, or pumice.

9. Process of claim 1, wherein said mixture is employed and 3-methyl piperdine is 0.01 to 98% by weight thereof.

* * * * *